United States Patent [19]

Fischer et al.

[11] 4,092,146

[45] May 30, 1978

[54] COMPOSITIONS, METHODS AND NEW COMPOUNDS FOR INFLUENCING PLANT GROWTH

[75] Inventors: Hanspeter Fischer, Bottmingen; Daniel Bellus, Riehen, both of Switzerland

[73] Assignee: Ciba-Geigy Corporation, Ardsley, N.Y.

[21] Appl. No.: 674,708

[22] Filed: Apr. 7, 1976

[30] Foreign Application Priority Data

Apr. 18, 1975  Switzerland .......................... 4995/75
May 30, 1975  Switzerland .......................... 6996/75

[51] Int. Cl.$^2$ .............................................. A01N 9/24
[52] U.S. Cl. ............................................ 71/70; 71/76; 71/88; 71/105; 71/122; 71/123; 260/340.3; 260/586 R
[58] Field of Search ........................... 71/123, 122, 70; 260/586 R

[56] References Cited

U.S. PATENT DOCUMENTS

| | | | |
|---|---|---|---|
| 2,349,772 | 5/1944 | ter Horst | 71/123 |
| 2,855,439 | 10/1958 | Kundiger et al. | 71/123 |
| 2,894,989 | 7/1959 | Pratt et al. | 71/123 |
| 2,908,692 | 10/1959 | Richert | 71/123 |
| 3,737,298 | 6/1973 | Fielding | 71/123 |
| 3,803,240 | 4/1974 | Durden et al. | 71/123 |

OTHER PUBLICATIONS

Maahs, "Preparations and reactions of, etc.;" (1965) CA 63, pp. 11373–11375 (1965).
Cohen et al., "Preparation and Reactions of, etc." (1965) J.A.C.S. 88, pp. 1533–1536 (1965).

*Primary Examiner*—Glennon H. Hollrah
*Attorney, Agent, or Firm*—Frederick H. Rabin

[57] ABSTRACT

Certain esters of 1-hydroxy-cyclobutene-3,4-dione and mono- and diesters of square acid have been found to be useful in the regulation of plant growth, especially as post-emergent herbicides, as plant growth inhibitors and desiccants.

New esters of this type and their manufacture are also described.

12 Claims, No Drawings

COMPOSITIONS, METHODS AND NEW COMPOUNDS FOR INFLUENCING PLANT GROWTH

The present invention provides herbicidal and plant growth-regulating compositions which contain as active component cyclobutenedione esters, for example esters of 1-hydroxy-cyclobutenedione and mono- or diesters of "square acid", and a method of using these compositions as contact herbicides for post-emergent, in particular selective, weed control and for regulating plant growth, especially for desiccation and reducing the length in growth of grasses and cereals.

The base compound corresponding to the cyclobutenedione esters, 1-hydroxy-cyclobutene-3,4-dione ("moniliformin") is an acid and its sodium salt and manufacture are known (Berichte der deutsch. Chem. Ges. Vol. 104, 873 (1971); Am. Soc. 96, 2267 (1974); Angewandte Chemie 86, 567 (1974). Its isolation as natural substance from a fungus (Fusarium moniliforme) and its phytotoxic (necrotic and chlorotic) and inhibiting action on plant growth are described in "Science" 179, 1324 (1973); but the constitution of the compound was not recognised according to this publication.

The manufacture of the methyl ester, 1-methoxy-cyclobutene-3,4-dione, is also described without any indication of activity in Am. Soc. 96, 2267 (1974).

Also known are 1,2-dihydroxy-cyclobutene-3,4-dione, also known as "square acid", salts thereof, the dichloride and many of the monoenol and dienol ethers, which are herein referred to as esters on account of the acid character of the hydroxyl group, as well as the manufacture thereof. The following publications may be cited:

Manufacture of the square acid: Angew. Chemie, 78, 927 (1966); Gazz, chim, ital. 102, 818 (1972).

Manufacture of derivatives and esters: Angewandte Chemie 75, 982 (1963), 78, 927 (1966); Annalen der Chemie 686, 55 (1965), 742, 116 (1970); Journal Amer. Chem. Soc. 88, 1533 (1966), 96, 3006 (1974); Tetrahedron Letters No. 10, 1970, p. 781. As related literature, attention is also directed to: Angewandte Chemie 81, 917 (1969), 84, 480 and 481 (1972), Berichte der deutsch. Chem. Gesellschaft 103, 3553 (1970) and DOS 1'518'660.

The present invention is based on the surprising observation that the already known mono- and diesters of square acid as well as further ones not yet described in the literature, and derivatives of these esters and certain new esters of monohydroxycyclobutenedione, possess excellent contact herbicidal properties and can be used both as total herbicides and especially as selective herbicides in crops of cultivated plants, and in addition possess plant growth-regulating properties, which make them suitable for use as desiccants and growth inhibitors, for example in grasses and types of cereal. These cyclobutenedione esters are markedly superior in their herbicidal action to the constitutionally similar 1-hydroxycyclobutene-3,4-dione and its salts ("moniliformin"), which is known as substance from B. 104, 873 (1971) and in its action from "Science" 179, 1324 (1973).

The herbicidal and plant growth-regulating composition of the present invention contains, in addition to carriers and additives and/or dispersants, as active component at least one cyclobutene-3,4-dione derivative of the formula I

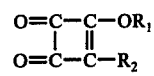

wherein

R₁ represents an alkyl radical of 1 to 12 carbon atoms which is unsubstituted or substituted by phenyl or substituted phenyl, halogen, cycloalkyl or lower alkoxy, or represents a cycloalkyl, alkenyl or alkinyl radical of at most 8 carbon atoms, or a phenyl radical which is unsubstituted or mono- or polysubstituted by halogen, alkyl, alkoxy, alkylthio, dialkylamino, nitro or cyano, R₂ represents hydrogen or a group —OR₃, wherein R₃ is a hydrogen ion or the equivalent of a metal cation or has the same meaning as R₁ above, and R₁ and R₃, besides the two adjacent oxygen atoms, can also represent the hydrocarbon bridge members of a 6- or 7-membered heterocyclic ring.

Preferably one or more of the following substituents are possible substituents of phenyl radicals in all positions (ortho, meta, para): halogen, for example fluorine, chlorine or bromine; lower alkyl, in particular methyl; lower alkoxy, in particular methoxy, and dialkylamino and nitro.

Alkyl radicals R₁ and R₃ can be straight-chain or branched; branched alkyl radicals contain preferably 3 to 8 carbon atoms.

If R₂ represents hydrogen, alkyl radicals R₁ preferably contain 4 to 12 carbon atoms. The preferred alkenyl radical is allyl. These esters of 1-hydroxycyclobutene-3,4-dione are markedly superior in their contact herbicidal and selective action and also in their plant growth regulating properties to the known base compound, 1-hydroxy-cyclobutene-3,4-dione.

However, among the active substances of the present invention, the square acid derivatives are preferred, that is to say those active substances of the formula I wherein R₂ represents a group —OR₃.

Preferred square acid derivatives are in turn those wherein each of R₁ and R₃ independently represents a straight-chain alkyl radical of 3 to 5 carbon atoms or a branched alkyl radical of up to 8 carbon atoms or a lower alkoxyalkyl radical.

New compounds of the general formula I which have not yet been described in the literature are those which have the narrower formula Ia

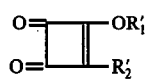

wherein

R₁' represents an alkyl radical of 2 to 12 carbon atoms which can be substituted — as indicated in formula I for R₁, a cycloalkyl, alkenyl or alkinyl radical or a substituted or unsubstituted phenyl radical, and R₂' represents hydrogen or a group —OR₃', wherein R₃' represents a branched alkyl radical of 4 to 8 carbon atoms or a substituted straight-chain or branched alkyl radical, a cycloalkyl, alkenyl or alkinyl radical or a substituted or unsubstituted phenyl radical, and R₁' and R₃' together can also represent a polymethylene radical of 3 or 4 carbon atoms.

Preferred new active substances of the formula Ia are those wherein $R_2'$ is the group $-OR_3'$, $R_1'$ represents a straight-chain alkyl radical of 3 to 5 carbon atoms or a branched alkyl radical of 4 to 8 carbon atoms, and $R_3'$ represents a branched alkyl radical of 4 to 8 carbon atoms or a straight-chain or branched alkyl radical which is preferably substituted by alkoxyalkyl.

The esters of the present invention of the formula I, wherein $R_2$ represents hydrogen, can be obtained by different processes:

(a) from the known base compound of the formula II

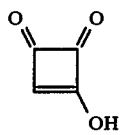

by heating with an alcohol of the formula $R_1'OH$, in which $R_1'$ is an aliphatic or araliphatic radical as defined in formula Ia, preferably in a solvent, such as benzene, and with continuous elimination of the water that forms during the reaction, or by transesterifying the known methyl ester by heating with an alkanol $R_1'OH$, preferably in the presence of an acid catalyst;

(b) by converting the base compound of the formula II with a chlorinating agent, for example $SOCl_2$, phosgene, oxalyl chloride etc., with or without a catalyst, such as dimethyl formamide, pyridine etc., into the active 1-chloro-cyclobutenedione, or by converting the base compound of the formula II with a lower alkanoic acid chloride $R_1'COCl$ or with a lower chlorocarbonate $ClCOOR_1'$ in the presence of an organic base, such as trialkylamine or pyridine, into the corresponding mixed anhydride, and reacting the intermediate with a compound $R_1OH$, in which $R_1$ is as defined in formula I;

(c) from an alkali salt of the base compound of formula II by reaction with an alkyl or aralkyl halide $R_1'Hal$, wherein $R_1'$ is as defined in (a).

In addition to being obtained by the processes mentioned hereinbefore, all of which are based on an acid-catalysed hydrolysis of a cyclobutane or cyclobutene (with an oxidation number = 6), the base compound of the formula II can also be obtained in principle from all structurally suitable cyclobutanes or cyclobutenes by a similar acid hydrolysis, for example: from 3,4,4-trialkoxycyclobuten-2-ones-1 which are obtained from tetraalkoxycyclobutanones [Berichte der deutsch. Chem. Ges. 104, 873 (1971)] for example by alcohol elimination catalysed by aluminium oxide (Angew. Chem. 87, 491 (1975); from 1,3-dichloro-2,2,3-trifluorocyclobutene which is obtained from the cycloadduct of trifluorochloroethylene with vinylidene chloride [J. Amer. Chem. Soc. 81, 2678 (1959)]; from 1-chloro-2,2,3,3-tetrafluorocyclobutene or its conversion product, 1-chlorotrifluoro-4-ethoxycyclobutene, the manufacture of which is described in J. Org. Chem. 28, 1008 (1963); from cycloadducts of dichlorovinylene carbonate with suitable olefins, such as 1,2-dichloroethylene, 1,1-dichloroethylene, 2,3-dihydro-p-dioxane, which are obtained by photochemical 2 + 2 additions as described in Angew. Chem. 86, 574 (1974); from the dimer of monochloroketone or the methyl enol ether thereof the syntheses of which are described in Chemistry Letters 1972, 927; finally from the bromination product of the 2 + 2 cycloadduct of ethyl vinyl ether and dichloroketene [J. Org. Chem. 32, 3703 (1967)].

(d) A method of obtaining preferred esters of the formula I, wherein $R_1$ represents an alkyl radical of 2 to 4 carbon atoms or the allyl radical, consists in the addition of gaseous carbomethylene (ketene) $CH_2=C=O$ to a tetrasubstituted ethylene of the formula III

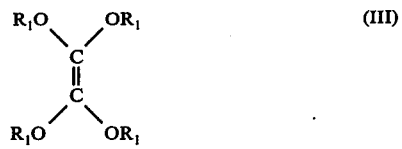

carbon atoms or allyl, to form a diketal

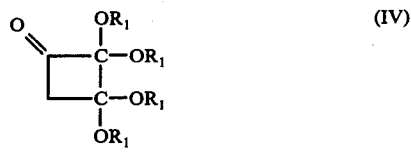

and in the subsequent acid "hydrolysis" thereof, to yield the desired cyclobutenedione ester of the formula I, in which $R_1$ represents alkyl of 2 to 4 carbon atoms or allyl, as well as the base compound of the formula II.

The addition of the ketene to the tetrasubstituted ethylene is carried out advantageously in an apparatus which is normally used for obtaining ketenes (e.g. "Org. Synthesis") at temperatures between $-20°$ C and $+80°$ C, preferably between $0°$ and $20°$ C, without a solvent or in the presence of aprotic solvents, such as n-pentane, hexane, octane, tetrahydrofuran, dioxan, ether, methylene chloride, benzene etc., the reaction time being dependent on the concentration of the gaseous ketene ($CH_2CO$).

The "hydrolysis" of the diketal IV (e.g. a 2,2,3,3-tetraalkoxybutanone(1)) is effected at temperatures of $20°-80°$ C (preferably $40°-80°$ C) until the reaction is complete (control), without a solvent or in the presence of aprotic solvents, such as those mentioned above, in the presence of acids, in particular of aqueous mineral acids, such as hydrochloric acid, sulphuric acid etc., or of concentrated carboxylic acids, for example formic acid ("formolysis") [Bull. Soc. Chim. France 1974, 529], or acetic acid etc., to yield the desired end product in addition to the base compound, 1-hydroxy-cyclobutene-3,4-dione.

The intermediate IV is preferably obtained by an improved modification of the process described in B. 104, 873 (1971) for the tetramethoxy derivative. The acid "hydrolysis" of the diketal IV by raising the temperature to above $20°$ C enables the manufacture of end products of the formula I in addition to the base compound of the formula II, which, according to this publication, was obtained as single end product from the tetramethoxy derivative.

The known square acid derivatives of the formula I, wherein $R_2$ is not hydrogen, are obtained in accordance with the particulars contained in the publications cited at the outset.

Where the square acid derivatives comprised by formula I have not yet been described, and this applies to those of the formula Ia, wherein $R_2' = OR_3'$, they are obtained in analogous fashion, for example from the free square acid by reaction with $SOCl_2$ to give the dichloride, which is reacted with one or two moles of the alcohol R₃'OH or with one mole of each of the different alcohols R₁'OH and R₃'OH; furthermore by direct monoesterification with an alcohol R₃'OH; or by transesterification of a square acid ester with another alcohol (Angew. Chemie 78, 927).

The following Examples 1 to 3 illustrate the processes for obtaining esters of 1-hydroxy-cyclobutenedione of formula Ia, wherein R₂' represents hydrogen.

The other Examples relate to the manufacture of square acid derivatives of the formula Ia, wherein R₂' is a group —OR₃'.

The table following these Examples lists further active substances which were obtained by one of the exemplified processes.

EXAMPLE 1

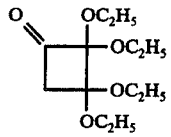

(a) Gaseous carbomethylene (CH₂=C=O) is passed into liquid 1,1,2,2-tetraethoxyethylene (86 g, 0.42 mole) until the infrared (IR) band of the olefin (wave number 1218 cm⁻¹) has completely disappeared. When producing this ketene in a standard apparatus, as described in J. Org. Chem. 5, 122 (1940), the reaction lasts 11 hours. The reaction vessel is cooled externally with ice-water while the ketene is being passed in. The crude reaction mixture is distilled in vacuo. The desired intermediate, 2,2,3,3-tetraethoxycyclobutanone-(1), is obtained from the fraction which boils at 63°–67° C/0.01 Torr after recrystallisation of the precipitated crystals from n-hexane.

Yield: 71.5 g (=69% of theory)
Melting point: 44°–45° C
IR spectrum (in KBr) = 1802, 1385, 1242, 1075, 928 and 832 cm⁻¹.
NMR (nuclear magnetic resonance spectrum) (in C₆D₆) = 1.10 + 1.13 (2xt, 12 H, 4 × CH₃), 2.78 (s, 2H, cyclobutane-CH₂), 3.0–4.1 ppm (m, 8H, 4 × —O—CH₂—).

Analysis for C₁₂H₂₂O₅ (molecular weight 246.31): calculated: C 58.51%; H 9.00%; O 32.48%. found: C 58.34%; H 9.12%; O 32.44%.

In addition to a further 6.4 g (=6% of theory) of the above compound, it is possible to isolate from the mother liquor by chromatography over silica gel (eluant = benzene/tetrahydrofuran 9:1) 6 g (=6.5% of theory) of 2,2-diethoxy-3-oxo-butyric acid ethyl ester as an oil with a boiling point of 90° C/0.1 Torr. IR spectrum (liquid) includes bands at: 1758, 1260, 1123 and 850 cm⁻¹.

(b)

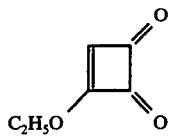

45 g of 2,2,3,3-tetraethoxycyclobutanone are stirred vigorously at 50° C in 4 normal aqueous HCl until the starting material is no longer detectable. The reaction solution is then extracted for 20 hours continuously with diethyl ether and the organic extracts are dried over MgSO₄ and concentrated. Precipitated crystals of 1-hydroxycyclobutene-3,4-dione are filtered off sharply and the liquid residue is distilled at 110° C/0.1 Torr to yield 6.65 g (=30% of theory) of the desired 1-ethoxycyclobutene-3,4-dione of the above structure.

IR (liquid): 1800, 1765, 1580, 1280, 1008 cm⁻¹.
NMR (in CDCl₃): 1.55 (t, CH₃), 4.55 (g, CH₂), 8.60

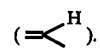

UV (in C₂H₅OH): λ max. = 356 nm (mμ).
Analysis for C₆H₆O₃ (molecular weight 126.11): calculated: C 57.11%; H 4.78%; O 38.05%. found: C 56.84%; H 4.90%; O 38.10%.

EXAMPLE 2

5.6 g of 1-methoxy-cyclobutene-3,4-dione [Am. Soc. 96, 2267 (1974)] and 0.05 g of p-toluenesulphonic acid are refluxed for 4 hours in 100 ml of absolute ethanol. After the alcohol has been distilled off, the liquid residue is distilled at 110° C/0.1 Torr to yield 5.1 g (=81% of theory) of the same end product as in Example 1b with the same analytical and physical characteristic data.

EXAMPLE 3

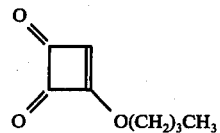

A suspension of 1.25 g of 1-hydroxycyclobutene-3,4-dione (A) in 10 ml of absolute n-butanol and 15 ml of benzene is heated to reflux in a Soxhlet apparatus. A passes slowly into solution. The water of reaction is bound to the molecular sieve 4A which is present in the apparatus. The reaction mixture is concentrated after 2 hours. The distillation of the residue at 105°–115° C/0.01 Torr yielded 1.6 g (=82% of theory) of 1-n-butoxycyclobutene-3,4-dione as a yellowish oil.

IR spectrum (liquid) includes bands at: 1800, 1775, 1580 and 1068 cm⁻¹.
NMR (in CDCl₃): 0.98 (t, 3H, CH₃), 1.2–2.2 (m. 4H, 2 × CH₃), 4.50 (t, 2H—OCH₂—) and 8.55 ppm (s, 1H,

Analysis for C₈H₁₀O₃ (molecular weight 154.16): calculated: C 62.32%; H 6.54%; O 31.44%. found: C 62.27%; H 6.68%; O 31.69%.

EXAMPLE 4

1,2-Di-(2-methyl-4-pentyloxy)-cyclobutenedione 11.4 g of square acid (0.1 mole) and 100 ml of 2-methyl-4-pentanol in 40 ml of absolute benzene are boiled for 16 hours at app. 110° C bath temperature in a steam trap. The resultant clear solution is concentrated by rotary evaporation and the residual oil is purified through a column of silica gel (80 cm × 4 cm, with hexane/acetone 2:1 as eluant).

Yield: 9.3 g of pure 1,2-di-(2-methyl-4-pentyloxy)-cyclobutenedione, $n_{20}^D = 1.4814$, and 12 g of a substance which contains square acid as impurity.

EXAMPLE 5

1,2-Diallyloxy-cyclobutenedione 11,4 g of square acid (0.1 mole), 100 ml of allyl alcohol and 50 ml of absolute benzene are boiled for 16 hours at app. 120° C bath temperature in a Soxhlet apparatus which is filled with app. 200 g of molecular sieve $A_4°$. The solution is then concentrated and the excess alcohol distilled off in a high vacuum at 50° C. The residual oil (17 g) is purified through a column of silica gel. Further drying in a high vacuum yields 13.4 g of 1,2-diallyloxy-cyclobutenedione ($n_D^{20} = 1.5275$). The yield is 70% of theory.

EXAMPLE 6

1,2-Di-(2-phenylethyloxy)-cyclobutenedione 17 g (0.1 mole) of 1,2-diethyloxy-cyclobutenedione, 48.8 g (0.4 mole) of 2-phenylethanol and some crystals of p-toluenesulphonic acid are boiled in a distillation apparatus until 9.5 ml of ethanol are distilled off. The residue is treated with hexane and filtered off. The filter residue is recrystallised from diisopropyl ether. The yield of pure 1,2-di-(2-phenylethyloxy)-cyclobutenedione is 20 g (m.p. 84°–85° C).

EXAMPLE 7

1-Butyloxy-2-(2-methoxyethyloxy)-cyclobutenedione 22.6 g of 1,2-dibutyloxy-cyclobutenedione (0.1 mole), 7.6 g (0.1 mole) of 2-methoxyethanol and some crystals of p-toluenesulphonic acid ae boiled for 26 hours at 100° C bath temperature. After the reaction mixture has been concentrated, the residual oil is distilled under a high vacuum. Distillation by means of a 5 cm Vigreux column yields 2.3 g (about 70%) of 1-butyloxy-2-(2-methoxyethyloxy)-cyclobutenedione (b.p. 137° C/0.02 Torr) with about 30% of 1,2-dibutyloxy-cyclobutenedione ($n_D^{20} = 1.4989$). As secondary fractions, 0.4 g of pure 1,2-dibutyloxy-cyclobutenedione and 18 g of a mixture consisting of app. 30% of 1-butyloxy-2-(2-methoxyethyloxy)-cyclobutenedione and app. 70% of starting material were obtained.

EXAMPLE 8

1,2-Di-(3-methoxyphenoxy)-cyclobutenedione 23.8 g (0.2 mole) of thionyl chloride are added dropwise to a suspension of 11.4 g (0.1 mole) of square acid in 60 ml of absolute benzene and 1 ml of dimethyl formamide in a 350 ml capacity flask. After heating to 100° C bath temperature, the reaction mixture is refluxed for 1½ hours, then cooled to room temperature and first 24.8 g of 3-methoxyphenol (0.2 mole) and then 22.2 g of triethylamine (0.22 mole) are added dropwise while cooling with ice. The reaction mixture is stirred for 16 hours at 120° C bath temperature and cooled once more. It is then concentrated and the residue is extracted, after it has been diluted with water, 8 times with ether. The ethereal extract is dried over $MgSO_4$ and evaporated. The crude product (29 g of red substance with a m.p. of app. 35°–40° C) is purified by column chromatography (silica gel 0.05–0.2 mm, 1 m × 4 cm, with hexane/acetone (2:1) as eluant). The resultant product is recrystallised from ether and 18 g of 1,2-di-(3-methoxyphenoxy)-cyclobutenedione with a melting point of 82°–83° C are isolated.

The following table lists further compounds of the formula I (known and new) which are obtained in analogous manner in addition to those described in the preceding Examples. All these compounds are soluble in conventional organic solvents, and many are prone to hydrolysis.

Active Substances

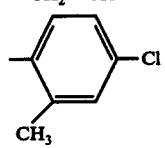

| Compound No. | $R_1$ | $R_2$ | Physical constants m.p. b.p./Torr/$n_D$ ° C |
|---|---|---|---|
| 1 | $CH_3$ | H | b.p.71° /0.04 Torr |
| 2 | $C_2H_5$ | H | b.p. 110° /0,1 |
| 3 | n-$C_4H_9$ | H | b.p. 110° /0,01 |
| 4 | n-$C_8H_{17}$ | H | b.p. 109° /0,02 |
| 5 | n-$C_{12}H_{25}$ | H | m.p.30° |
| 6 | $-CH_2-CH=CH_2$ | H | b.p.82° /0,04 |
| 7 | 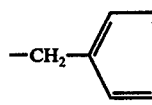 | H | m.p.86.5–87° |
| 8 | 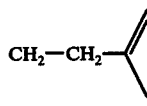 | H | m.p.98.5–99° |
| 9 | $CH_2-CH_2-$⌬ | H | m.p.62–62.5° |
| 10 | 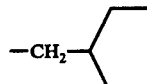 | H | m.p.36.5–37° |
| 11 | $CH_3$ | OH | m.p.81° |
| 12 | $CH_3$ | $-OCH_3$ | m.p.33° |
| 13 | $C_2H_5$ | $-OC_2H_5$ | b.p.91° /0,01 |

-continued

Active Substances $$\begin{array}{c} O= \\ O= \end{array} \begin{array}{c} R_2 \\ OR_1 \end{array}$$

| Compound No. | $R_1$ | $R_2$ | Physical constants m.p. b.p./Torr/$n_D$ ° C |
|---|---|---|---|
| 14 | n-$C_3H_7$ | —O-n$C_3H_7$ | b.p. 95°/0,01 |
| 15 | n-$C_4H_9$ | —O—$C_4H_9$(n) | b.p. 120°/0,01 |
| 16 | n-$C_5H_{11}$ | —O—$C_5H_{11}$(n) | b.p. 130°/0,001 |
| 17 | n-$C_6H_{13}$ | —O—$C_6H_{13}$(n) | b.p. 153°/0,001 |
| 18 | n-$C_{10}H_{21}$ | —O—$C_{10}H_{21}$(n) | b.p. > 160°/0,001 |
| 19 | i-$C_3H_7$ | —O—$C_3H_7$(i) | b.p. 110°/0,03 |
| 20 | sec. $C_4H_9$ | —O—$C_4H_9$(sec) | b.p. 115°/0,02 |
| 21 | iso-$C_4H_9$ | —O$C_4H_9$(i) | b.p. 118°/0,01 |
| 22 | —CH—$(CH_2)_2$—$CH_3$<br>\|<br>$CH_3$ | —O—CH$(CH_2)_2$—$CH_3$<br>\|<br>$CH_3$ | b.p. 111°/0,001 |
| 23 | —$CH_2$—CH—$C_2H_5$<br>\|<br>$CH_3$ | —O—$CH_2$—CH—$C_2H_5$<br>\|<br>$CH_3$ | b.p. 145°/0,001 |
| 24 | —$CH_2$—$CH_2$—CH$(CH_3)_2$ | —O—$CH_2$—$CH_2$—CH$(CH_3)_2$ | b.p. 140°/0,001 |
| 25 | —CH—$CH_2$—CH$(CH_3)_2$<br>\|<br>$CH_3$ | —O—CH—$CH_2$—CH$(CH_3)_2$<br>\|<br>$CH_3$ | $n_D$ = 1.4814 |
| 26 | —CH—CH—$C_2H_5$<br>\| \|<br>$CH_3$ $CH_3$ | —O—CH—CH—$C_2H_5$<br>\| \|<br>$CH_3$ $CH_3$ | $n_D$ = 1.4881 |
| 27 | —CH—$C_3H_7$(n)<br>\|<br>$C_2H_5$ | —O—CH—$C_3H_7$(n)<br>\|<br>$C_2H_5$ | $n_D$ = 1.4857 |
| 28 | —$CH_2$—CH$(C_2H_5)_2$ | —O—$CH_2$—CH$(C_2H_5)_2$ | $n_D$ = 1.4858 |
| 29 | —CH—CH$(C_2H_5)_2$<br>\|<br>$C_2H_5$ | —O—CH—CH$(C_2H_5)_2$<br>\|<br>$C_2H_5$ | $n_D$ = 1.4860 |
| 30 | Cyclopentyl | O-cyclopentyl | m.p. 73° |
| 31 | $C_2H_5$ | —O—$C_4H_9$(n) | b.p. 87°/0,001 |
| 32 | $C_2H_5$ | —O—$CH_2$—C≡CH | $n_D$ = 1.5206 |
| 33 | —$C_4H_9$(n) | —O—$CH_2$—$CH_2$—$OCH_3$ | b.p. 135°/0,02 |
| 34 | —$C_4H_9$(n) | —O—$CH_2$—CH—$C_2H_5$<br>\|<br>$CH_3$ | b.p. 117°/0,01 |
| 35 | —$CH_2$—CH=CH—$CH_3$ | —O—$CH_2$—CH=CH—$CH_3$ | b.p. 115°/0,001 |
| 36 | —$CH_2$—C≡CH | —O—$CH_2$—C≡CH | $n_D$ = 1.5415, decomp. 110°/0,01 |
| 37 | —$CH_2$—$CH_2$—CH=$CH_2$ | —O—$CH_2$—$CH_2$—CH=$CH_2$ | b.p. 150°/0,02 |
| 38 | —$CH_2$—CH=$CH_2$ | —O—$CH_2$—CH=$CH_2$ | $n_D$ = 1.5275 |
| 39 | —$CH_2$—$CH_2$—C≡CH | —O—$CH_2$—$CH_2$—C≡CH | $n_D$ = 1.5326 |
| 40 | —$CH_2$—$CH_2$—O—$CH_3$ | —O—$CH_2$—$CH_2$—O—$CH_3$ | b.p. 150°/0,001 |
| 41 | —$(CH_2)_3$Cl | —O—$(CH_2)_3$Cl | $n_D$ = 1,5356 |
| 42 | —$(CH_2)_4$Cl | —O—$(CH_2)_4$Cl | $n_D$ = 1,5155 |
| 43 | —$(CH_2)_3$Br | —O$(CH_2)_3$Br | m.p. 52° |
| 44 | —$CH_2$—$CH_2$—C$_6$H$_5$ | —O—$CH_2$—$CH_2$—C$_6$H$_5$ | m.p. 85° |
| 45 | —$CH_2$—$(CF_2)_3$CHF$_2$ | —O—$CH_2$—$(CF_2)_3$CHF$_2$ | |
| 46 | phenyl | —O-phenyl | m.p. 165° |
| 47 | 2,4-dichlorophenyl | —O-(2,4-dichlorophenyl) | oily-crystalline |
| 48 | 2-methoxyphenyl | —O-(2-methoxyphenyl) | m.p. 86° |
| 49 | (cyclic dioxo-dioxolane structure) | | $n_D$ = 1,5526<br>m.p. = 142–144° |

The compounds of the present invention of the formula I possess herbicidal, in particular contact herbicidal, action, and can be used as total herbicides or as selective agents for post-emergent use for combating weeds in different crops of cultivated plants.

In addition to their use as contact herbicides for total and selective weed control, the active substances and compositions that contain them are also suitable for the desiccation and defoliation, for example, of potatoes and cotton, and a number of them have also a plant growth-regulating action, for example growth inhibition in grasses and cereals, fruit abscission (e.g. compound 11), sucker control in tobacco plants, and permeability changes in the plant cells. A number of the compounds of formula I also possess marked fungicidal and bactericidal properties (e.g. compound 22), and others also have an insecticidal action (e.g. compounds 4 and 5).

In all these spheres of action the compounds of the formula I are markedly superior to 1-hydroxy-cyclobutene-3,4-dione and the sodium salt thereof whose phytotoxic and growth-regulating action is described in "Science" 179, 1324 (1973), and also to the amine derivatives of DOS 1'518'660.

The good contact herbicidal action of the compounds is particularly evident, for example, in Lolium, Solanum, Sinapis and other varieties of weed.

When used as herbicides, the compounds are preferably applied after the emergence of the weeds and cultivated plants (post-emergent treatment). The rates of application are in the usual range between 1 and 10 kg per hectare.

The compositions of the present invention are obtained in known manner by intimately mixing and grinding active substances of the general formula I with suitable carriers and/or additives, optionally with the addition of antifoam agents, wetting agents, dispersants and/or solvents which are inert to the active substances. The active substances may take and be used in the following forms:
  solid forms: dusts, in particular tracking agents and granulates, for example coated granulates, impregnated granulates and homogeneous granulates;
  active substance concentrates which are dispersible in water: wettable powders, pastes, emulsions, emulsifiable concentrates;
  liquid forms: solutions.

The concentration of active substance in the compositions of this invention is between 1 and 80 percent by weight. As circumstances may require, the active substances can also be applied in low concentrations of about 0.05 to 1 percent by weight.

The compositions of the present invention can be mixed with other biocidal active substances or compositions. Thus in addition to containing the cited compounds of the formula I, the compositions of the present invention can also contain, for example, insecticides, fungicides, bactericides, fungistatic agents, bacteriostatic agents, nematocides or further herbicides, in order to broaden the activity spectrum. It is also advantageous to add light stability agents.

On account of a certain proneness to hydrolysis, it is desirable to formulate the active substances in the anhydrous state or to add dehydrating agents to them.

Granules

The following substances are used to manufacture 5% granules:
  5 parts of one of the active substances of the formula I, e.g. compound 4,
  0.25 parts of epichlorohydrin,
  0.25 parts of cetyl polyglycol ether,
  3.50 parts of polyethylene glycol,
  91 parts of kaolin (particle size 0.3 – 0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to manufacture (a) a 70% and (b) a 10% wettable powder:
  (a) 70 parts of one of the active substances of the formula I, e.g. compound 5
    5 parts of sodium dibutylnaphthalene sulphate,
    3 parts of naphthalenesulphonic acid/phenolsulphonic acid/formaldehyde condensate (3:2:1),
    10 parts of kaolin,
    12 parts of Champagne chalk;
  (b) 10 parts of square acid dibutyl ester,
    3 parts of a mixture of the sodium salts of saturated fatty alcohol sulphates,
    5 parts of naphthalenesulphonic acid/formaldehyde condensate.
    82 parts of kaolin.

The respective active substance is applied to the corresponding carriers (kaolin and chalk) and then these are mixed and ground, to yield wettable powders of excellent wettability and suspension power. By diluting these wettable powders with water it is possible to obtain suspensions containing 0.1 to 8% of active substance. These suspensions are suitable for combating weeds in cultivations of plants.

Paste

The following substances are used to manufacture a 45% paste:
  45 parts of square acid di-n-butyl ester or one of the other active substances of the formula I,
  5 parts of sodium aluminium silicate,
  14 parts of cetyl polyglycol ether with 8 moles of ethylene oxide,
  1 part of oleyl polyglycol ether with 5 moles of ethylene oxide,
  2 parts of spindle oil,
  10 parts of polyethylene glycol,
  23 parts of water.

The active substance is intimately mixed with the additives in appropriate devices and ground. A paste is obtained from which, by dilution with water, it is possible to manufacture suspensions of every desired concentration of active substance.

Emulsion concentrate

The following ingredients are mixed to manufacture a 25% emulsion concentrate:
  25 parts of square acid diethyl ester or of one of the other active substances of the formula I
  5 parts of a mixture of nonylphenolpolyoxyethylene and calcium dodecylbenzenessulphonate,
  35 parts of 3,5,5-trimethyl-2-cyclohexen-1-one,
  35 parts of dimethyl formamide.

This concentrate can be diluted with water to give emulsions in suitable concentrations of e.g. 0.1 to 10%. Such emulsions are suitable for combating weeds in cultivations of plants.

Herbicidal action in the post-emergence application of the active substances

The weeds *Sinapis alba, Stellaria media, Lolium perenne, Setaria litalica* and tomato, oat and edible bean plants are sprayed, when in the 4 to 6 leaf stage, with an aqueous active substance emulsion (obtained from a 25% emulsifiable concentrate) in a concentration of 4 kg of active substance per hectare. The plants are then kept at 24° to 26° C and 45 to 60% relative humidity.

The experiment is evaluated 14 days after the treatment. The evaluation is made using the rating from 1-9:

9 = plants undamaged (control)
1 = plants withered
8-2 = intermediate stages of damage Composition of the emulsifiable concentrate: 25 parts of active substance, 32.5 parts of methyl ethyl ketone, 32.5 parts of 3,5,5-trimethyl-2-cyclohexen-1-one and 10 parts of a mixture of nonylphenolpolyoxyethylene and calcium dodecylsulphonate.

Results

| Compound No. | Weeds | | | |
|---|---|---|---|---|
| | Setaria italica | Lolium perenne | Sinapis alba | Stellaria media |
| Moniliformin, sodium salt square acid (comparison substance) | 4 | 7 | 6 | 4 |
| 2 | 6 | 9 | 5 | 8 |
| | 3 | 7 | 3 | 3 |
| 4 | 1 | 4 | 1 | 2 |
| 5 | 3 | 5 | 3 | 3 |
| 15 | 2 | 3 | 1 | 2 |
| 24 | 3 | 3 | 1 | 2 |
| 31 | 1 | 4 | 1 | 2 |
| 33 | 3 | 4 | 1 | 2 |
| 37 | 3 | 3 | 1 | 2 |
| 40 | 1 | 6 | 1 | 1 |

Compared with the known sodium salt of 1-hydroxy-cyclobutene-3,4-dione (moniliformin), the evaluation of the experiment showed that 1-ethoxy-cyclobutene-3,4-dione (compound 2) has a markedly better contact herbicidal action against the weeds Stellaria, Setaria and Sinapis with equally good protection of the oat plant (*Avena sative*, rating 8-9) and also exerts a more pronounced desiccation effect on leaves (experimental result on beans).

In comparison with moniliformin and with the free square acid, all the active substances of this invention of the square acid series (compounds from 11 onwards) possess a markedly better contact herbicidal action against the cited weeds. In particular, *Sinapis alba* and *Stellaria media* and almost totally destroyed by nearly all the square acid esters of this invention. This desiccation effect on bean leaves is also clearly more pronounced.

We claim:

1. A method for controlling the growth of weeds which comprises applying thereto a herbicidally effective amount of a compound of the formula

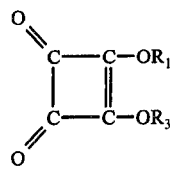

in which
$R_1$ is alkyl of from 1 to 12 carbon atoms; or alkyl of from 1 to 12 carbon atoms substituted by fluorine, chlorine, bromine or methoxy; and
$R_3$ is a hydrogen ion, an equivalent metal cation or a group falling within the definition of $R_1$.

2. A method according to claim 1 in which $R_1$ is alkyl of from 4 to 12 carbon atoms.

3. A method according to claim 1 in which $R_3$ is alkyl selected from the group consisting of a straight chain alkyl having from 3 to 5 carbon atoms, a branched alkyl having from 3 to 8 carbon atoms, and a methoxy substituted derivative of said alkyl.

4. A method according to claim 3 in which the compound is 1,2-di-n-propoxy-cyclobutenedione.

5. A method according to claim 3 in which the compound is 1,2-di-n-butoxy-cyclobutenedione.

6. A method according to claim 3 in which the compound is 1,2-di-n-pentyloxy-cyclobutenedione.

7. A method for defoliating and desicating plants which comprises applying thereto an effective amount of a compound of the formula

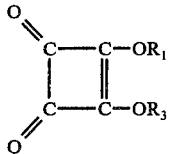

in which
$R_1$ is alkyl of from 1 to 12 carbon atoms; or alkyl of from 1 to 12 carbon atoms substituted by fluorine, chlorine, bromine or methoxy; and
$R_3$ is a hydrogen ion, an equivalent metal cation or a group falling within the definition of $R_1$.

8. A method according to claim 7 in which $R_1$ is alkyl of from 4 to 12 carbon atoms.

9. A method according to claim 7 in which $R_3$ is alkyl selected from the group consisting of a straight chain alkyl having from 3 to 5 carbon atoms, a branched alkyl having from 3 to 8 carbon atoms, and a methoxy substituted derivative of said alkyl.

10. A method according to claim 9 in which the compound is 1,2-di-n-propoxy-cyclobutenedione.

11. A method according to claim 9 in which the compound is 1,2-di-n-butoxy-cyclobutenedione.

12. A method according to claim 9 in which the compound is 1,2-di-n-pentyloxy-cyclobutenedione.

* * * * *